(12) United States Patent
Nagai et al.

(10) Patent No.: US 7,906,042 B2
(45) Date of Patent: Mar. 15, 2011

(54) BRANCHED SURFACTANT HAVING FLUOROALKYL GROUP AND HYDROCARBON GROUP

(75) Inventors: Takabumi Nagai, Tsukuba (JP); Kazuhisa Fujii, Tsukuba (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/696,694

(22) Filed: Jan. 29, 2010

(65) Prior Publication Data
US 2010/0176345 A1    Jul. 15, 2010

Related U.S. Application Data

(62) Division of application No. 11/596,672, filed as application No. PCT/JP2005/008893 on May 16, 2005.

(30) Foreign Application Priority Data

May 20, 2004  (JP) .................................. 2004-149934
Jun. 21, 2004  (JP) .................................. 2004-183077

(51) Int. Cl.
    *B01F 1/00*  (2006.01)
(52) U.S. Cl. .................... 252/364; 510/108; 510/492
(58) Field of Classification Search ................. 252/364; 510/108, 492
    See application file for complete search history.

(56) References Cited

U.S. PATENT DOCUMENTS

| | | | |
|---|---|---|---|
| 3,137,713 A | 6/1964 | Kwan-Ting et al. | |
| 5,877,796 A | 3/1999 | Tsuchiya et al. | |
| 6,589,723 B2 | 7/2003 | Yamanouchi et al. | |
| 7,144,688 B2 | 12/2006 | Nakagawa et al. | |
| 7,258,970 B2 | 8/2007 | Yoshioka et al. | |
| 2002/0197571 A1 | 12/2002 | Yamanouchi et al. | |
| 2003/0072716 A1* | 4/2003 | Poovathinthodiyil et al. | 424/43 |
| 2003/0203330 A1 | 10/2003 | Yoshioka | |
| 2004/0044244 A1 | 3/2004 | Yamanouchi et al. | |

FOREIGN PATENT DOCUMENTS

| | | |
|---|---|---|
| CA | 1053058 | 4/1979 |
| EP | 1 283 440 A1 | 2/2003 |
| EP | 1 345 074 A1 | 9/2003 |
| JP | 50-161236 A | 12/1975 |
| JP | 51-32322 A | 3/1976 |
| JP | 52-25087 B | 7/1977 |
| JP | 52-26687 B | 7/1977 |
| JP | 58-184151 A | 10/1983 |
| JP | S61-159636 A | 7/1986 |
| JP | 62-265651 | 11/1987 |
| JP | S63-289547 A | 11/1988 |
| JP | H07-311450 A | 11/1995 |
| JP | 09-030114 | 2/1997 |
| JP | 9-30114 A | 2/1997 |
| JP | 2002-255921 | 9/2002 |
| JP | 2003-029368 A | 1/2003 |
| JP | 2003-57780 A | 2/2003 |
| JP | 2003-107617 A | 4/2003 |
| JP | 2003/107647 A | 4/2003 |
| JP | 2003-113155 | 4/2003 |
| JP | 2003-114502 A | 4/2003 |
| JP | 2003-149766 A | 5/2003 |
| JP | 2003-149774 A | 5/2003 |
| JP | 2003-322927 A | 11/2003 |
| JP | 2004-018394 A | 1/2004 |
| JP | 2004-125995 A | 4/2004 |
| JP | 2004/126262 A | 4/2004 |
| JP | 2004-157468 A | 6/2004 |
| JP | 2004-287133 A | 10/2004 |
| JP | 2004-354461 A | 12/2004 |
| JP | 2005-043475 A | 2/2005 |

OTHER PUBLICATIONS

Translation of JP 51-032322.*
Eastoe, et al., "Progr Colloid Polym Sci. 2000, 115, 214-221—Springer-Verlag 2000 Adsorption of Fluoro Surfactants" at Air-Water and Water-Carbon Dioxide Interfaces.
Liu, et al., "Water in Carbon Dioxide Microemulsions with Fluorinated Analogues of AOT"—Langmuir 2001, 17, pp. 274-277.
Sagisaka, et al.., "Preparation of A W/CO2 Microemulsion Using Fluorinated Surfactants"—Langmuir, 2003, vol. 19, pp. 220-225.
Harrison, et. al., "Water-in-Carbon Dioxide Microemulsions With A Fluorocarbon-Hydrocarbon Hybrid Surfactant"—Langmuir, 1994, vol. 10, pp. 3536-3541.

(Continued)

*Primary Examiner* — Mark Kopec
*Assistant Examiner* — Haidung D Nguyen
(74) *Attorney, Agent, or Firm* — Sughrue Mion, PLLC

(57) ABSTRACT

The present invention relates to a surfactant represented by Formula (I):

[Formula 1]

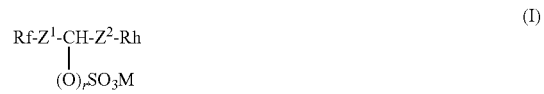

wherein Rf represents a fluoroalkyl group which may have an ether bond;
Rh represents an alkyl group;
r represents 1 or 0;
when r=0, $Z^1$ and $Z^2$ represent $(CH_2)_{n1}$—$(X^1)_{p1}$— and —$(X^2)_{q1}$—, respectively; and
when r=1, $Z^1$ and $Z^2$ represent $(CH_2Y)_{p2}$—$CH_2$— and —$(CH_2Y)_{q2}$—, respectively,
wherein $X^1$ and $X^2$ may be the same or different and each represents a divalent linking group,
p1 represents 0 or 1,
q1 represents 0 or 1,
n1 represents an integer of 1-10;
Y represents O, S or NR, wherein R represents a hydrogen atom, methyl, ethyl, n-propyl, isopropyl, n-butyl, isobutyl, sec-butyl, or t-butyl;
p2 and q2 each represent 0 or 1 but are not 0 at the same time; and
M represents a hydrogen atom, alkali metal, ½ alkaline earth metal or ammonium.

11 Claims, 1 Drawing Sheet

OTHER PUBLICATIONS

Yoshino, et. al., "Syntheses of Hybrid Anionic Surfactants Containing Fluorocarbon and Hydrocarbon Chains"—Langmuir, 1995, vol. 11, pp. 466-469.

Kondo et al., :Synthesis of Fluorocarbon-Hydrocarbon Hybrid Surfactans Having a Phospate Group—JAWC 2000 Abstracts NST, p. 305.

Kondo et al., "Synthesis of Fluorocarbon-Hydrocarbon Hybrid Surfactants Having A Sulfate Group"—JAWC 2000 Abstracts NST, p. 306.

Kondo et al., "First Anionic Micelle with Unusually Long Lifetime: Self-Assembly of Fluorocarbon-Hydrocarbon Hybrid Surfactant"—J. Am. Chem. Socl., 2002, vol. 124, pp. 6516-6517, 2002.

Keiper et. al., "New Phosphate Fluorosurfactants of Carbon Dioxide"—J. Am. Chem. Soc., 2002, vol. 124, p. 1834.

Kondo et al., "Synthesis and Physical Properties of New Hybrid Gemini Surfactant—Processing of Yukagaku Toronkai", Abstract, p. 101, 2002.

Haruhiko, M, et. al., "Synthesis and Solution Properties of Sulfate-Type Hybrid Surfactants with an Ethylene Spacer", Journal of Oleo Science, vol. 54, No. 3, 167-178.

Jain, M, et. al., "Active-site directed specific competitive inhibitors of phospholipase $A_2$: Novel Transition-State Analogues", Biochemistry 1991, 30(42), 10256-68 Coden: Bichaw; ISSN: 0006-2960, 1991.

Supplementary European Search Report Jun. 3, 2008.

Nagai, T, et al., "Water in Supercritical $CO_2$ Microemulsion Formulation by Fluorinated Surfactants", Chemistry Letters, vol. 32, No. 4, pp. 220-225(2003).

Japanese Office Action for JP 2004-149934 dated Dec. 9, 2009.

Japanese Office Action for JP 2004-183077 dated Dec. 9, 2009.

* cited by examiner

Put a sample in portion "a"

BRANCHED SURFACTANT HAVING FLUOROALKYL GROUP AND HYDROCARBON GROUP

This is a divisional of application Ser. No. 11/596,672 filed Jan. 29, 2007, which is a National Stage Application filed under §371 of PCT Application No. PCT/JP2005/008893 filed May 16, 2005. The entire disclosures of the prior applications are hereby incorporated by reference.

TECHNICAL FIELD

The present invention relates to a branched surfactant having a fluoroalkyl group and a hydrocarbon group.

The surfactant of the invention, when used in combination with liquid, subcritical, or supercritical carbon dioxide, can improve the function of carbon dioxide as a solvent for chemical reactions, washing, extraction, dyeing, etc.

BACKGROUND OF THE INVENTION

Due to increasing awareness of environmental problems, attention has been drawn to techniques using $CO_2$ as a solvent in place of highly toxic organic solvents. If it makes it possible to dissolve a compound in $CO_2$, the cost of wastewater treatment may be sharply reduced. Therefore, attention has been drawn particularly to the application of such techniques to industrial fields which require expensive waste water treatments, such as dyeing, plating, organic synthesis, chemical reaction, washing, extraction, etc.

Such applications need surfactants to mix carbon dioxide with polar compounds.

Examples of hybrid fluorine-based compounds having both a hydrocarbon group and a fluoroalkyl group in the molecule are mentioned as follows: Patent Document 1 discloses $H(CF_2CF_2)_n(CH_2CH_2O)_nOOCCH(OSO_3Na)CH_2COOR$ as an additive for improving the application properties of a light-sensitive material; Patent Document 2 discloses $H(CF_2CF_2)_nCH_2OCH_2CH(OSO_3Na)R$ as an additive for improving the application properties of a light-sensitive material; and Patent Document 3 discloses $H(CF_2CF_2)_nCH_2OCH_2CH(OSO_3Na)CH_2OR$ as an antistatic material for a light-sensitive material.

Surfactants that function well in carbon dioxide are extremely limited. For example, only sulfosuccinic acid esters having fluorine groups, which require two hydrophobic chains or branched hydrophobic group, are reported in Non-patent Documents 1 to 3. Non-patent Document 4 reports that $C_7F_{15}CH(OSO_3Na)C_7H_{15}$ has a high ability to incorporate water into carbon dioxide. However, due to low stability, this compound has not been put into practical use. Moreover, a test performed by the present inventors confirmed that the water-uptake ability of this compound is insufficient.

In view of the above, the synthesis of a hybrid surfactant with stability and an advanced function has been reported in recent years (Non-patent Documents 5 to 8). However, these known hybrid surfactants do not fulfill their functions in carbon dioxide (Non-patent Document 3).

Although phosphates as reported in Non-patent Document 9 function well in carbon dioxide, phosphates have problems with stability during long-term use due to the possibility of hydrolysis. A test performed by the present inventors confirmed that phosphates also do not fulfill their functions satisfactorily.

Patent Document 1: Japanese Unexamined Patent Publication No. 1976-32322
Patent Document 2: Japanese Examined Patent Publication No. 1977-25087
Patent Document 3: Japanese Examined Patent Publication No. 1977-26687
Non-patent Document 1: Progr, Colloid Polym, Sci., 2000, vol. 115, page 214
Non-patent Document 2: Langmuir, 2001, vol. 17, page 274
Non-patent Document 3: Langmuir, 2003, vol. 19, page 220
Non-patent Document 4: Langmuir, 1994, vol. 10, page 3536
Non-patent Document 5: Langmuir, 1995, vol. 11, page 466
Non-patent Document 6: Proceeding of Yukagaku Toronkai, 2000 (Abstract, pages 305 and 306)
Non-patent Document 7: Proceeding of Yukagaku Toronkai, 2002 (Abstract, page 101)
Non-patent Document 8: J. Am. Chem. Soc., 2002, vol. 124, page 6516
Non-patent Document 9: J. Am. Chem. Soc., 2002, vol. 124, page 1834

DISCLOSURE OF THE INVENTION

Problem to be Solved by the Invention

An object of the invention is to provide a surfactant usable in a carbon dioxide-water system.

Means for Solving the Problem

The invention provides the following surfactants.

Item 1. A surfactant represented by Formula (I):

[Formula 1]

wherein Rf represents a fluoroalkyl group which may have an ether bond;

Rh represents an alkyl group;

r represents 1 or 0;

when r=0, $Z^1$ and $Z^2$ represent $(CH_2)_{n1}$—$(X^1)_{p1}$— and —$(X^2)_{q1}$—, respectively; and when r=1, $Z^1$ and $Z^2$ represent $(CH_2Y)_{p2}$—$CH_2$— and —$(CH_2Y)_{q2}$—, respectively, wherein $X^1$ and $X^2$ may be the same or different and each represents a divalent linking group, p1 represents 0 or 1, q1 represents 0 or 1, n1 represents an integer of 1-10;

Y represents O, S or NR, wherein R represents a hydrogen atom, methyl, ethyl, n-propyl, isopropyl, n-butyl, isobutyl, sec-butyl, or t-butyl;

p2 and q2 each represent 0 or 1 but are not 0 at the same time; and

M represents a hydrogen atom, alkali metal, ½ alkaline earth metal or ammonium.

Item 2. A surfactant represented by Formula (IA) according to item 1:

[Formula 2]

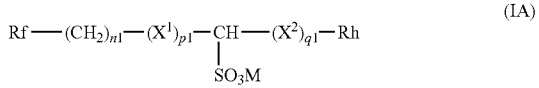

(IA)

wherein Rf represents a fluoroalkyl group which may have an ether bond;
Rh represents an alkyl group;
$X^1$ and $X^2$ may be the same or different and each represents a divalent linking group,
p1 represents 0 or 1,
q1 represents 0 or 1,
n1 represents an integer of 1-10; and
M represents a hydrogen atom, alkali metal, ½ alkaline earth metal or ammonium.

Item 3. A surfactant represented by Formula (IB) according to item 1:

[Formula 3]

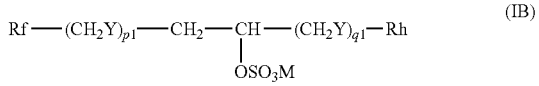

(IB)

wherein Rf represents a (per)fluoroalkyl group, (per)fluoroether group, or (per)fluoropolyether group;
Rh represents an alkyl group;
Y represents O, S, or NR, wherein R represents a hydrogen atom, methyl, ethyl, n-propyl, isopropyl, n-butyl, isobutyl, sec-butyl, or t-butyl;
p2 and q2 each represent 0 or 1 but are not 0 at the same time; and
M represents a hydrogen atom, alkali metal, ½ alkaline earth metal or ammonium.

Item 4. A surfactant according to claim 1, wherein Rf has 5 to 12 carbon atoms.

Item 5. A surfactant according to item 2 represented by Formula: $Rf(CH_2)_{n1}OOCCH(SO_3M)CH_2COORh$,
wherein Rf, Rh, n1, and M are as defined above.

Item 6. A surfactant according to item 2 represented by Formula: $Rf(CH_2)_{n1}OCCH(SO_3M)Rh$,
wherein Rf, Rh, n, and M are as defined above.

Item 7. A surfactant according to item 3 represented by Formula: $RfCH_2OCH_2CH(OSO_3M)CH_2ORh$,
wherein Rf, Rh, and M are as defined above.

Item 8. Use of a surfactant according to item 1 for adding to a system comprising carbon dioxide and a polar compound.

Item 9. Use of a surfactant according to item 8, wherein the polar compound is water.

Item 10. Use of a surfactant according to item 1 for improving solubility of a polar compound in supercritical, subcritical, or liquid carbon dioxide.

Effect of the Invention

The present invention provides a surfactant with a high ability to incorporate water into carbon dioxide despite water having a low compatibility with carbon dioxide. Thus, the use of the surfactant of the invention in a carbon dioxide-polar compound system achieves a well-mixed state of water and carbon dioxide.

Moreover, the invention can provide a surfactant having a sufficiently high water-uptake value and a sufficient ability to form micelles in a mixed system of $CO_2$/water and a polar compound (e.g., inorganic salt, polar organic compound, etc.).

BEST MODE FOR CARRYING OUT THE INVENTION

Figure 1A:
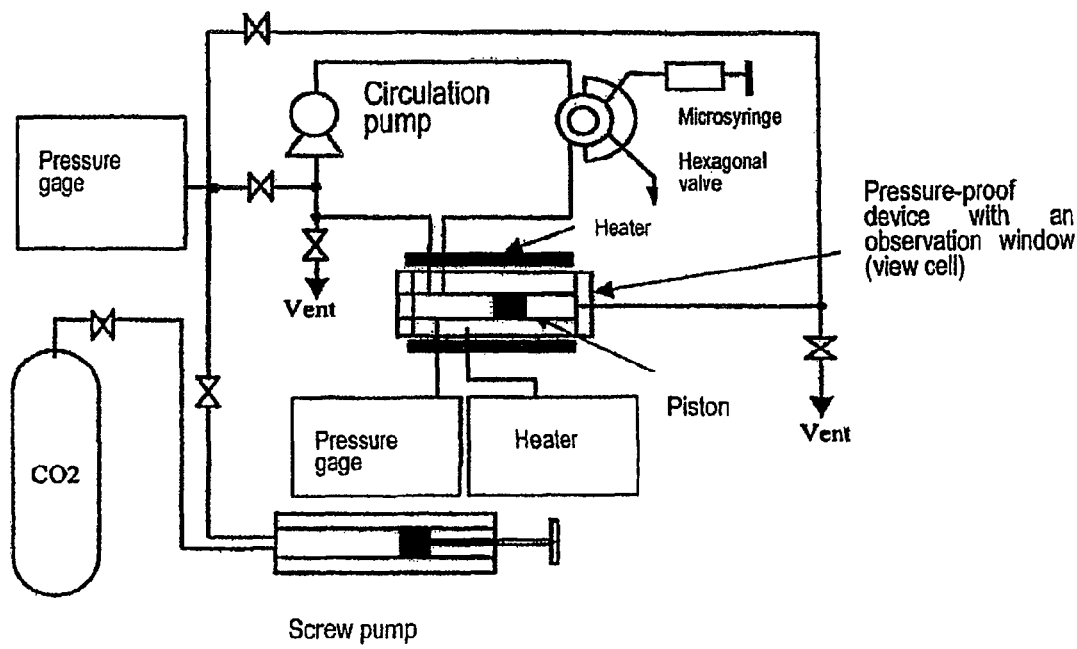
FIG. 1(A) is a view schematically showing a device for determining W values.

The surfactants of the invention make it possible to mix $CO_2$ (supercritical, subcritical, or liquid) with polar compounds, such as water. Moreover, the surfactants of the invention can improve, using $CO_2$ as a solvent, the efficiency of electrochemical reactions, and also washing, dyeing, extraction, etc. The electrochemical reactions refer to organic/inorganic chemical reactions, plating, etc., in which a polar compound, such as water and the like, is treated. In addition, the surfactants of the invention have stability enough to withstand repeated use in $CO_2$-water systems.

Preferable as such surfactants are hybrid surfactants having a sulfate group or a sulfonic acid group, and also one fluoroalkyl group and one alkyl group.

Examples of polar compounds to be mixed with a $CO_2$ solvent include water; organic solvents miscible with water such as alcohols (e.g., methanol, ethanol, propanol, butanol, etc.), water-containing alcohols, DMF, DMSO, formamide, glycols (e.g., ethylene glycol, propylene glycol, etc.), acetonitrile, THF, etc.; or mixtures of water and these organic solvents. Among these, water is preferable. Furthermore, metal particles, inorganic salts, organic salts, bio-compounds (e.g., phospholipids, saccharides, proteins, carbohydrates, etc.), etc. can be mentioned.

In the surfactants represented by Formula (I), Rf represents a linear or branched fluoroalkyl group which may have an ether bond. Specific examples thereof include (per)fluoroalkyl groups, (per)fluoroether groups, and (per)fluoropolyether groups. Rf has 4 to 50 carbon atoms. The number of carbons of a fluoroalkyl group in which Rf has no ether bond is 4 to 20, preferably 5 to 18, and more preferably 5 to 12. The number of carbons of a fluoroalkyl group in which Rf has an ether bond is 4 to 50, preferably 5 to 40, and more preferably 5 to 35.

When r=0, preferable examples of Rf are as follows. Preferable examples of fluoroalkyl groups having no ether bond include:

$C_mF_{2m+1}$—(n represents an integer of 4 to 20 and m represents an integer of 1 to 10); and
$HC_mF_{2m}$—(n represents an integer of 4 to 20 and m represents an integer of 1 to 10).

Preferable examples of fluoroalkyl groups having an ether bond include:

$C_mF_{2m+1}O(CF_2CF_2O)_rCF_2$—(m represents an integer of 1 to 10 and r represents an integer of 1 to 15);
$C_mF_{2m+1}O(CF(CF_3)CF_2O)_rCF(CF_3)$—(m represents an integer of 1-10 and r represents an integer of 1 to 15);
$HC_mF_{2m}O(CF_2CF_2O)_rCF_2$—(m represents an integer of 1 to 10 and r represents an integer of 1 to 15); and
$HC_mF_{2m}O(CF(CF_3)CF_2O)_rCF(CF_3)$—(M represents an integer of 1 to 10 and r represents an integer of 1 to 15).

Preferable examples of Rf among the compounds represented by Formula (I) in which r=1 are as follows.

Examples of (per)fluoroalkyl groups include:

$C_nF_{2n+1}(CH_2)_m$—(n represents an integer of 5 to 12 and m represents an integer of 1 to 10); and $HC_nF_{2n}(CH_2)_m$—(n represents an integer of 5 to 12 and m represents an integer of 1 to 10).

Examples of (per)fluoroether groups include Rf1-O—Rf2, such as $C_3F_7OCF(CF_3)$— and the like, wherein Rf1 is a $C_{1-6}$ linear or branched (per)fluoroalkyl group and Rf2 is a $C_{1-4}$ linear or branched (per)fluoroalkylene group.

Examples of (per)fluoropolyether groups include Rf1-(O—Rf2)$_r$, such as $C_3F_7OCF(CF_3)CF_2OCF(CF_3)$— and the like, wherein (Rf1 and Rf2 are as defined above and r represents an integer of 2 to 4).

Rh is a linear or branched alkyl group having 3 to 18 carbon atoms, preferably 4 to 12, and more preferably 4 to 10. Specific preferable examples of Rh include (n-, sec-, iso-, tert-) butyl, pentyl, hexyl, heptyl, octyl, nonyl, and decyl.

In order to achieve a balance between a portion that has affinity with $CO_2$ (Rf) and a hydrophilic group (Rh), the value obtained by dividing the number of carbon atoms of Rf by the number of carbon atoms of Rh is preferably in the range of 1/2 to 2/1, and more preferably in the range of 2/3 to 3/2.

M represents a hydrogen atom, alkali metal (Na, K, Li, Cs), ½ alkaline earth metal (Ca, Mg, Ba), ammonium ($NH_4$), or quaternary ammonium ($NR_4$; R represents a $C_{1-4}$ linear or branched alkyl group).

When r=0, $Z^1$ and $Z^2$ represent $(CH_2)_{n1}$—$(X^1)_{p1}$— and —$(X^2)_{q1}$—, respectively. Examples of divalent linking groups represented by $X^1$ and $X^2$ include O, S, NH, NR, C=O, C(O)O, OC(O), C(O)S, SC(O), C(O)NH, C(O)NR, NH(O)C, NR(O)C (wherein R is a $C_{1-4}$ linear or branched alkyl group). Between $X^1$ and/or $X^2$ and $CH(SO_3M)$ may be positioned a linear or branched alkylene group which may be fluorinated (e.g., $(CH_2)_m$, $(CF_2)_n$, $CF(CF_3)$, $(CF_2)_n(CH_2)$, etc., m and n are integers of 1 to 3).

Preferable divalent linking groups represented by $X^1$ and $X^2$ are mentioned as follows:

—$(CH_2)_n$COO—(n is an integer of 0 to 4, preferably 0 or 1) and —$(CH_2)_n$O—(n is an integer of 0 to 4, preferably 0 or 1), wherein p1 is 0 or 1; q1 is 0 or 1; n1 is an integer of 1 to 10, preferably 1 to 5; when r=1, $Z^1$ and $Z^2$ represent $(CH_2Y)_{p2}$—$CH_2$— and —$(CH_2Y)_{q2}$—, respectively; Y is O, S, or NR (R represents a hydrogen atom, methyl, ethyl, n-propyl, isopropyl, n-butyl, isobutyl, sec-butyl, or t-butyl), preferably O or NR, and more preferably O; and p2 and q2 represent 0 or 1 but are not 0 at the same time.

The surfactants of the invention are commercially available or can be easily produced by a person skilled in the art according to known methods (e.g., Patent Documents 1 to 3).

In the invention, the amount of surfactant is about 0.001 to about 2000 wt %, preferably about 0.01 to about 1000 wt %, more preferably about 0.01 to about 500 wt %, and particularly preferably about 0.1 to about 100 wt % based on the amount of polar compound to be dissolved in an aqueous solution or carbon dioxide.

In addition, an organic solvent (co-solvent) described below can be added to a $CO_2$-water system. For example, alcohols such as methanol, ethanol, propanol, butanol, pentanol, etc.; ketones such as acetone and the like; acetonitrile; esters such as ethyl acetate, etc.; ethers such as ethyl ether; halogenated compounds such as frons, methylene chloride, chloroform, etc. Among these, organic solvents with low toxicity and low molecular weight are preferable.

Unlike the case where surfactants are used in normal two-phase systems, the weight of the surfactant for use in the invention may be higher than that of a polar compound depending on the kind of the polar compound. For example, in the case of chemical reaction using a metal salt or the like as a catalyst in $CO_2$, the amount of surfactant sometimes exceeds 100 wt %.

The surfactant of the invention is preferably used in a two-phase system between $CO_2$ (liquid, subcritical, or supercritical state) and water or a polar compound.

EXAMPLES

Hereinafter, the present invention will be described with reference to Examples and Reference Examples in detail, but is not limited thereto.

(A) Surfactants Having a Sulfonate Group (r=0 in Formula (I))

Examples 1A to 5A

Following the description of Japanese Unexamined Patent Publication No. 1976-32322, compounds 1A-5A were synthesized.

The physical properties of the obtained compounds are as follows:

1A: $C_6F_{13}CH_2CH_2OOCCH(SO_3Na)CH_2COOC_6H_{13}$
Colorless and Amorphous:
$^1$H-NMR ($CD_3OD$): δ 0.90 (t, J=6.9 Hz, 3H), 1.19-1.50 (m, 6H), 1.50-1.75 (m, 2H), 2.45-2.79 (m, 2H), 2.93-3.27 (m, 2H), 4.00-4.22 (m, 3H), 4.34-4.50 (m, 2H).
IR (KBr, cm$^{-1}$): 2968, 1740, 1241, 1209, 1146, 1033.

2A: $C_6F_{13}CH_2CH_2OOCCH(SO_3Na)CH_2COOC_8H_{17}$
Colorless and Amorphous:
$^1$H-NMR ($CD_3OD$): δ 0.94 (t, J=7.3 Hz, 3H), 1.27-1.50 (m, 10H), 1.50-1.73 (m, 2H), 2.45-2.80 (m, 2H), 2.94-3.38 (m, 2H), 4.00-4.20 (m, 3H), 4.33-4.50 (m, 2H).
IR (KBr, cm$^{-1}$): 2969, 1737, 1241, 1146, 1054.

3A: $C_8F_{17}CH_2CH_2OOCCH(SO_3Na)CH_2COOC_{10}H_{21}$
Colorless and Amorphous:
$^1$H-NMR($CD_3OD$): δ 0.89 (t, J=6.8 Hz, 3H), 1.15-1.45 (m, 14H), 1.50-1.75 (m, 2H), 2.45-2.79 (m, 2H), 2.94-3.27 (m, 2H), 4.02-4.22 (m, 3H), 4.36-4.51 (m, 2H).
IR (KBr, cm$^{-1}$): 2930, 1741, 1245, 1220, 1153, 1055.

4A: $C_8F_{17}CH_2CH_2OOCCH(SO_3Na)CH_2COOC_6H_{13}$
Colorless and Amorphous:
$^1$H-NMR ($CD_3OD$): δ 0.91 (t, J=6.9 Hz, 3H), 1.20-1.50 (m, 6H), 1.50-1.76 (m, 2H), 2.44-2.80 (m, 2H), 2.94-3.47 (m, 2H), 4.02-4.20 (m, 3H), 4.33-4.52 (m, 2H).
IR (KBr, cm$^{-1}$): 2967, 1740, 1244, 1210, 1152, 1054.

5A: $C_4F_9CH_2CH_2OOCCH(SO_3Na)CH_2COOC_4H_9$
Colorless and Amorphous:
$^1$H-NMR($CD_3OD$): δ 0.94 (t, J=7.3 Hz, 3H), 1.25-1.50 (m, 2H), 1.50-1.73 (m, 2H), 2.45-2.80 (m, 2H), 2.94-3.37 (m, 2H), 4.02-4.22 (m, 3H), 4.33-4.50 (m, 2H).
IR (KBr, cm$^{-1}$): 2967, 1739, 1229, 1135, 1054.

Comparative Examples 1A-5A

Compounds (6A to 8A) having two fluoroalkyl groups were synthesized according to Bull. Chem. Soc. Jpn., 1991, vol. 64, page 3262. Compound 9A was synthesized in the same manner as described above using an alcohol compound $C_4F_9CH_2CH_2CH_2CH_2OH$ obtained by reducing, with lithium aluminum hydride, a product obtained by radical addition reaction between $C_4F_9I$ with $CH_2=CHCH_2CH_2OH$. Furthermore, compound 10A was synthesized according to Langmuir 1994, 10, 3536.

The structures and compound numbers are shown below.
6A: $H(CF_2)_4CH_2OOCCH(SO_3Na)CH_2COOCH_2(CF_2)_4H$
7A: $H(CF_2)_6CH_2OOCCH(SO_3Na)CH_2COOCH_2(CF_2)_6H$
8A: $F(CF_2)_8CH_2CH_2OOCCH(SO_3Na)CH_2COOCH_2CH_2(CF_2)_8F$
9A: $F(CF_2)_4(CH_2)_4OOCCH(SO_3Na)CH_2COO(CH_2)_4(CF_2)_4F$
10A: $C_7F_{15}CH(OSO_3Na)C_7H_{15}$ Physical Properties of Compound 9A
  Colorless and Amorphous:
  $^1$H-NMR(CD$_3$OD): δ 1.56-1.90 (m, 8H), 2.05-2.38 (m, 4H), 2.95-3.28 (m, 2H), 4.02-4.30 (m, 5H).
  IR (KBr, cm$^{-1}$): 2968, 1738, 1224, 1134, 1051.

Test Example 1A

A functional test was performed on the compounds obtained in Examples and Comparative Examples.
(1) Method for Determining a W Value and Amount of Water Uptake
  Using an experimental apparatus shown in FIG. 1, the W value and amount of water uptake were determined according to the following processes 1 to 4.
1) A surfactant was placed in a proportion of 2 wt % based on the proportion of carbon dioxide in portion "a" of a pressure-proof device with an observation window (i.e., view cell).
2) After carbon dioxide was introduced and the pressure and temperature were adjusted as specified in Table 1A, water was introduced into portion "a" from a hexagonal valve.
3) When the visual observation of the contents through the observation window (sapphire window) showed that the mixture was transparent single phase, it was judged that water dissolved in carbon dioxide.
4) The W value and amount of water uptake were calculated from the highest amount of water uptake possible for maintaining a colorless state, and from the weight of the surfactant used for measurement.

The adjusted measurement pressures and temperatures of item 2) above are shown in Table 1A, in which surfactant effects were evaluated based on the ability of each surfactant to incorporate water into carbon dioxide: the W value=(the number of water molecules/the number of surfactant molecules) in a micelle; and water uptake=the weight of water dissolved in carbon dioxide, per gram of surfactant.

TABLE 1A

| Compound Number | W value (measurement pressure and temperature) | Water uptake |
| --- | --- | --- |
| 1A | 30 (33 MPa, 50° C.) | 0.9 g |
| 2A | 30 (33 MPa, 50° C.) | 0.9 g |
| 4A | 30 (24 MPa, 50° C.) | 0.7 g |
| 6A | 7 (31 MPa, 50° C.) | 0.2 g |
| 7A | 15 (26 MPa, 56° C.) | 0.3 g |
| 8A | 30 (34 MPa, 50° C.) | 0.5 g |
| 9A | 9 (17 MPa, 50° C.) | 0.2 g |
| 10A | 0 (33 MPa, 50° C.) | 0 g |

Compound 10A has been reported to be unstable but have advanced function (Langmuir 1994, 10, 3536). However, a test performed by the present inventors showed that compound 10A did not fulfill its function at all. This is probably because the test was performed at 50° C. under the same conditions as in other compounds. After the test, the samples were collected so as to determine the cause by instrumental analysis (NMR). The analysis showed that, small but complicated peaks were observed (decomposition possibly progressed even at 50° C.) in addition to the fact that the sulfate was hydrolyzed, which possibly forms a serious obstacle to the practical use of compound 10A.

Although compounds 7A to 8A have been reported to be stable and function best (Langmuir, 2001, vol. 17, page 274; Langmuir, 1997, vol. 13, page 6980), compounds 1A to 4A of the invention function better than compounds 7A to 8A.

The evaluation results show that compound 9A does not have high ability of water uptake, even if two carbon chains each have a fluoroalkyl chain and a hydrocarbon chain, and thus the number of carbon atoms in each of fluoroalkyl and hydrocarbon chains is eight in total, respectively.

Next, a mixture of compound 6A and AOT:$C_8H_{17}$OOCCH(SO$_3$Na)CH$_2$COOC$_8H_{17}$, which is sulfosuccinic acid ester having only a hydrocarbon group in the molecule, in a molar ratio of 1:1 was examined.

As shown below, the results of the examination of the mixture are the same as those obtained with only compound 6A, whose number of molecules is half that of the mixture. This shows that the desired function cannot be achieved by mixing a compound having two hydrocarbon groups with a compound having two fluoroalkyl groups, and that unless the compound has both a fluoroalkyl group and a hydrocarbon group in the molecule, such compound cannot exhibit the advanced function of the invention.

TABLE 2A

| Compound Number | W value | Water uptake |
| --- | --- | --- |
| Compound 6A and AOT (molar ratio of 1:1) | 7 (31 MPa, 50° C.) | 0.2 g (based on the amount of Compound 6A) |
| Compound 6A | 7 (31 MPa, 50° C.) | 0.2 g |

The above results reveal that a branched hybrid sulfonate, which has, in the molecule, both a fluoroalkyl group whose carbon number of one carbon chain is at least four and a hydrocarbon chain whose carbon chain length is nearly equal to that of the fluoroalkyl group, function well when a polar compound, such as water, is dissolved in carbon dioxide.

(B) Surfactant Group Having a Sulfonate Group (r=1 in Formula (I))

Example 1B

1B: $C_8F_{17}CH_2CH(OSO_3Na)CH_2OC_8H_{17}$

A mixture of heptadecafluoropropylene oxide (1.09 g, 2.3 mmol), octanol (1.02 g, 7.8 mmol), and one drop of sulfuric acid was heated at 100° C. for 48 hours under stirring. The result was extracted with ethyl acetate, and the organic layer was washed with saturated aqueous sodium bicarbonate and brine. The washed matter was dried with magnesium sulfate, and the solvent was then distilled off under reduced pressure. The reactant obtained was isolated by silica gel column chromatography (n-hexane:EtOAc=30:1), yielding an alcohol compound (830 mg, 60%). To the alcohol compound obtained was added a SO$_3$-Py complex (416 mg, 2.6 mmol). The mixture was stirred in 5 ml of pyridine at 40° C. for 24 hours. The reactant was placed in saturated aqueous bicarbonate, and heated to dryness. Inorganic salt was removed from the remaining reactant by extraction with acetone using a Soxhlet extractor, yielding compound 1B (730 mg, two steps, 45%).

Colorless and Amorphous:
$^1$H-NMR (CDCl$_3$): δ 0.88 (t, J=6.5 Hz, 3H), 1.15-1.47 (m, 10H) 1.47-1.65 (m, 2H), 2.47-2.87 (m, 2H), 3.35-3.62 (m, 2H), 3.62-3.78 (m, 2H), 4.74-4.90 (m, 1H).
IR: (KBr, cm$^{-1}$): 2934, 1243, 1213, 1152, 951.

Example 2B

2B: $C_6F_{13}CH_2CH(OSO_3Na)CH_2OC_6H_{13}$

Tridecafluoro propylene oxide (5.0 g, 13.3 mmol) and hexanol (8.35 ml, 66.5 mmol) were reacted in the presence of sulfuric acid, giving an alcohol compound (3.5 g, 55%). A $SO_3$-Py complex (2.3 g, 14.6 mmol) was reacted with this alcohol compound in pyridine (12 ml). Inorganic salt was removed from the rough product by extraction with acetone using a Soxhlet extractor, yielding compound 2B (3.1 g, two steps, 40%).

Colorless and Amorphous:
$^1$H-NMR(CDCl$_3$): δ 0.89 (t, J=6.8 Hz, 3H), 1.15-1.44 (m, 7H), 1.44-1.68 (m, 2H), 2.40-2.86 (m, 2H), 3.32-3.76 (m, 4H), 4.70-5.0 (m, 1H).
IR (KBr, cm$^{-1}$): 2936, 1244, 1214, 1150.

Example 3B

3B: $H(CF_2)_6CH_2OCH_2CH(OSO_3Na)CH_2OC_6H_{13}$

In the same manner as in Example 1B, compound 3B (3.1 g, two steps, 52%) was synthesized from dodecafluoroheptyl glycidyl ether (3.88 g, 10 mmol) and hexanol (2.94 g, 30 mmol).

Colorless and Amorphous:
$^1$H-NMR(CDCl$_3$): δ 0.89 (t, J=7.0 Hz, 3H), 1.22-1.40 (m, 6H), 1.49-1.60 (m, 2H), 3.43-3.52 (m, 2H), 3.60-3.69 (m, 2H), 3.85 (d-d, J=10.9, 4.4 Hz, 1H), 3.92 (d-d, J=10.9, 4.4 Hz, 1H), 4.13 (t, J=14.1 Hz, 2H), 4.45-4.52 (m, 1H), 6.61 (t-t, J=50.8, 4.9 Hz, 1H).
IR (KBr, cm$^{-1}$): 2938, 1240, 1202, 1142, 1045, 797.

Example 4B

4B: $H(CF_2)_8CH_2OCH_2CH(OSO_3Na)CH_2OC_8H_{17}$

In the same manner as in Example 1B, an alcohol compound was synthesized from hexadecafluoroheptyl glycidyl ether (8.06 g, 16.5 mmol) and octanol (13 ml, 82.3 mmol), and sulfonate compound 4B (5.0 g, two steps, 42%) was then synthesized from the alcohol compound.

Colorless and Amorphous:
$^1$H-NMR (CD$_3$OH): δ 0.89 (t, J=6.9 Hz, 3H), 1.15-1.46 (m, 10H) 1.46-1.65 (m, 2H), 3.48 (t, J=6.4 Hz, 2H), 3.60-3.75 (m, 2H), 3.80-4.00 (m, 2H), 4.16 (t, J=14.1 Hz, 2H), 4.43-4.55 (m, 1H), 6.69 (t-t, J=51.1 Hz, 5.1 Hz, 1H).
IR (KBr, cm$^{-1}$): 2936, 1214, 1149, 1043, 806.

Example 5B

5B: $H(CF_2)_6CH_2OCH_2CH(OSO_3Na)CH_2OC_8H_{17}$

In the same manner as in Example 1B, an alcohol compound was synthesized from dodecafluoroheptyl glycidyl ether (5.92 g, 15.2 mmol) and octanol (12 ml, 76 mmol), and compound 5B (4.2 g, two steps, 45%) was then synthesized from a $SO_3$-Py complex via the alcohol compound.

Colorless and Amorphous:
$^1$H-NMR(CD$_3$OH): δ 0.89 (t, J=6.9 Hz, 3H), 1.17-1.47 (m, 10H), 1.47-1.66 (m, 2H), 3.45 (t, J=6.4 Hz, 2H), 3.60-3.74 (m, 2H), 3.80-4.00 (m, 2H), 4.15 (t, J=14.1 Hz, 2H), 4.43-4.55 (m, 1H), 6.65 (t-t, J=51.1, 5.1 Hz, 1H).
IR (KBr, cm$^{-1}$): 2936, 1202, 1142, 1043, 796.

Example 6B

6B: $C_3F_7OCF(CF_3)CH_2OCH_2CH(OSO_3Na)CH_2OCH_2CH(C_2H_5)C_4H_9$

In the same manner as in Example 1B, an aqueous sodium hydroxide solution (1.3 g of NaOH and 6.3 ml of water) was added dropwise at 90° C. under stirring to a mixture of 2-ethylhexyl glycidyl ether (6.55 ml, 31.6 mmol) and 2-heptafluoro-propoxy-2,3,3,3-tetrafluoro propanol (10.0 g, 32 mmol), and the mixture was reacted for 6 hours. The reaction liquid was extracted with ethyl acetate, the organic phase was dried, and the solvent was distilled off, giving an alcohol compound. Compound 6B (6.76 g, two processes, 35%) was synthesized from this alcohol compound using a $SO_3$-Py complex.

Colorless Liquid:
$^1$H-NMR(CD$_3$OH): δ 0.80-1.00 (m, 6H), 1.15-1.65 (m, 9H), 3.34 (d, J=5.6 Hz, 2H), 3.42 (d-d, J=5.1, 1.5 Hz, 2H), 3.50-3.76 (m, 2H), 3.76-3.91 (m, 1H), 4.19 (d, J=11.9 Hz, 2H).
IR (KBr, cm$^{-1}$): 2933, 1239, 1150, 998.

Example 7B

7B: $C_3F_7OCF(CF_3)CH_2OCH_2CH(OSO_3Na)C_6H_{13}$

In the same manner as in compound 5B, an alcohol compound was synthesized from 1,2-epoxyoctane (4.83 ml, 31.6 mmol) and 2-heptafluoro-propoxy-2,3,3,3-tetrafluoropropanol (10.0 g, 32 mmol), and compound 7B (9.8 g, two steps, 56%) was then synthesized via the alcohol compound using a $SO_3$-Py complex.

Colorless and Amorphous:
$^1$H-NMR(CD$_3$OH): δ 0.87 (t, J=7.0 Hz, 3H), 1.15-1.55 (m, 8H) 1.55-1.77 (m, 2H), 3.75-3.89 (m, 2H), 4.08-4.30 (m, 2H), 4.30-4.46 (m, 1H).
IR (KBr, cm$^{-1}$): 2936, 1336, 1236, 1151, 997, 936.

Comparative Example 1B

8B: $(C_6F_{13}CH_2CH_2O)_2P(O)ONa$

Compound 8B was synthesized according to J. Am. Chem. Soc., 2002, vol. 124, page 1834.

Comparative Example 2B

9B: $C_7F_{15}CH(OSO_3Na)C_7H_{15}$

Compound 9B was synthesized according to J. Phys. Chem., 1992, vol. 96, page 6738.

Test Example 1B

A functional test was performed on the compounds obtained in Examples and Comparative Examples.

(1) Method for Determining a W Value and Amount of Water Uptake

Figure 1B:
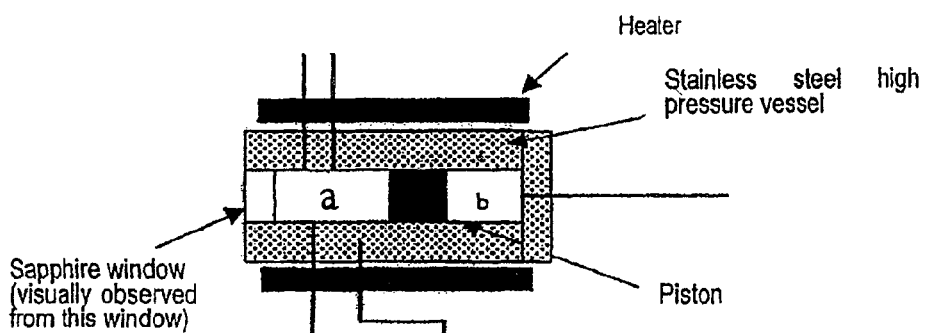
FIG. 1(B) is a view showing a view cell in detail, in which a sample is placed in portion "a".

Using a measuring device shown in FIG. 1, the W value and water uptake were determined according to the following processes 1 to 4.

1) A surfactant was placed in a proportion of 2 wt % based on the proportion of carbon dioxide in portion "a" of a pressure-proof device with an observation window (i.e., view cell).

2) After carbon dioxide was introduced and the pressure and temperature were adjusted as specified in Table 1B, water was introduced into portion "a" from a hexagonal valve.

3) When the visual observation of the contents through the observation window (sapphire window) showed that the mixture was colorless and homogeneous, it was judged that water dissolved in carbon dioxide.

4) The W value and amount of water uptake were calculated from the highest amount of water uptake possible for maintaining a colorless state, and from the weight of the surfactant used for measurement.

The adjusted measurement pressures and temperatures of item 2) above are shown in Table 1B, in which surfactant effects were evaluated based on the ability of each surfactant to incorporate water into carbon dioxide: the W value=(the number of water molecules/the number of surfactant molecules) in a micelle; and water uptake=weight of water dissolved in carbon dioxide, per gram of surfactant.

TABLE 1B

Water uptake = the weight of water dissolved in carbon dioxide per gram of surfactant

| Compound Number | W value (measurement conditions) | Water uptake |
|---|---|---|
| 2B (Example 2B) | 41 (33 MPa, 33° C.) | 1.3 g |
| 3B (Example 3B) | 40 (33 MPa, 33° C.) | 1.3 g |
| 5B (Example 5B) | 40 (25 MPa, 50° C.) | 1.2 g |
| 6B (Example 6B) | 37 (24 MPa, 50° C.) | 1.1 g |
| 8B (Comparative Example 1B) | 14 (19 MPa, 50° C.) | 0.3 g |
| 9B (Comparative Example 2B) | 0 (33 MPa, 50° C.) | 0 g |

Compounds 8B and 9B have been reported to function best (J. Am. Chem. Soc., 2002, vol. 124, page 1834; Langmuir, 1994, vol. 10, page 3536), and these publications describe that the amount of water uptake of these compounds reaches one gram per gram of surfactant, which is the highest water uptake value reported until now. However, the amount of water uptake of each of compounds 2B, 3B, 5B, and 6B of the present invention is larger than that of compound 8B or 9B.

The present inventors synthesized and evaluated compounds 8B and 9B under the same conditions as the compounds of the invention. The evaluation results show that although compound 8B fulfilled its function at relatively low pressure, the water uptake of compound 8B was notably lower than that of the reported data.

On the other hand, compound 9B did not fulfill its function at all, probably because the test was performed at 50° C. After the test, samples were collected so as to determine the cause by instrumental analysis (NMR). The analysis confirmed that small but complicated peaks were observed (decomposition possibly progressed even at 50° C.) in addition to the fact that the sulfate was hydrolyzed, which possibly forms a serious obstacle to practical use of compound 9B.

In contrast, it was confirmed that the compounds of the invention fulfill their functions stably under the conditions of the evaluation test (after the evaluation test, samples were collected and confirmed by an instrumental analysis).

As is clear from the above, the compounds of the invention are surfactants that demonstrate excellent properties in dissolving polar compounds, such as water, in a medium comprising carbon dioxide as a solvent.

The invention claimed is:

1. A composition comprising a surfactant represented by Formula (IA), carbon dioxide selected from the group consisting of supercritical, subcritical, and liquid carbon dioxide, and a polar compound,

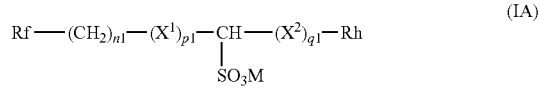

(IA)

wherein Rf represents a fluoroalkyl group, optionally having an ether bond;

Rh represents an alkyl group;
$X^1$ and $X^2$ are the same or different and each represents a divalent linking group,
p1 represents 0 or 1,
q1 represents 0 or 1,
n1 represents an integer of 1 to 10; and
M represents a hydrogen atom, alkali metal, ½ alkaline earth metal or ammonium.

2. The composition according to claim 1, wherein the Rf in the surfactant represented by the Formula (IA) has 5 to 12 carbon atoms.

3. The composition according to claim 1, wherein the surfactant is represented by Formula: $Rf(CH_2)_{n1}OOCCH(SO_3M)CH_2COORh$.

4. The composition according to claim 1, wherein the surfactant is represented by Formula: $Rf(CH_2)_{n1}C(=O)CH(SO_3M)Rh$.

5. The composition according to claim 1, wherein the amount of the surfactant is 0.001 to 2,000 wt. % relative to the amount of the polar compound.

6. The composition according to claim 1, wherein the surfactant represented by the Formula (IA) has the value obtained by dividing the number of carbon atoms of Rf by the number of carbon atoms of Rh in the range of 1/2 to 2/1.

7. The composition according to claim 1, wherein the polar compound is at least one member selected from the group consisting of water, metal particles, inorganic salts, organic salts, phospholipids, saccharides, proteins, and carbohydrates.

8. The composition according to claim 1, wherein the polar compound is water.

9. A method of dissolving a polar compound in carbon dioxide, wherein the carbon dioxide is selected from the group consisting of supercritical, subcritical, and liquid carbon dioxide, wherein the method comprises the steps of:
mixing the carbon dioxide, the polar compound, and a surfactant represented by Formula (IA),

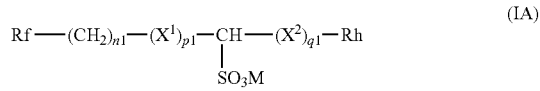

(IA)

wherein Rf represents a fluoroalkyl group, optionally having an ether bond;
Rh represents an alkyl group;
$X^1$ and $X^2$ are the same or different and each represents a divalent linking group,
p1 represents 0 or 1,
q1 represents 0 or 1,
n1 represents an integer of 1 to 10; and
M represents a hydrogen atom, alkali metal, ½ alkaline earth metal or ammonium,
under the condition where the carbon dioxide is selected from the group consisting of supercritical, subcritical, and liquid carbon dioxide.

10. A method of producing a composition comprising a surfactant represented by Formula (IA), carbon dioxide selected from the group consisting of supercritical, subcritical, and liquid carbon dioxide, and a polar compound comprising the step of:
mixing the surfactant represented by the Formula (IA), carbon dioxide, and the polar compound under the condition where the carbon dioxide is selected from the group consisting of supercritical, subcritical, and liquid form;

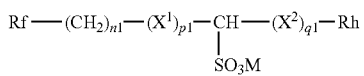

(IA)

wherein Rf represents a fluoroalkyl group, optionally having an ether bond;
Rh represents an alkyl group;
$X^1$ and $X^2$ are the same or different and each represents a divalent linking group,
p1 represents 0 or 1,
q1 represents 0 or 1,
n1 represents an integer of 1 to 10; and
M represents a hydrogen atom, alkali metal, ½ alkaline earth metal or ammonium.

11. A method of dissolving a polar compound in carbon dioxide comprising the steps of:
(i) placing a known amount of surfactant in a pressure-proof device;
(ii) introducing $CO_2$ into the device and adjusting the pressure and temperature of the device to be between 24 and 33 MPa and 33 and 50° C., respectively; and
(iii) introducing said polar compound into the pressure-proof device until a single phase is formed; and
wherein said surfactant is represented by Formula (IA):

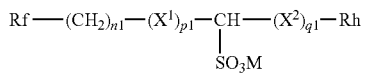

(IA)

wherein Rf represents a fluoroalkyl group, optionally having an ether bond;
Rh represents an alkyl group;
$X^1$ and $X^2$ are the same or different and each represents a divalent linking group,
p1 represents 0 or 1,
q1 represents 0 or 1,
n1 represents an integer of 1 to 10; and
M represents a hydrogen atom, alkali metal, ½ alkaline earth metal or ammonium.

* * * * *